United States Patent [19]

Zasloff et al.

[11] Patent Number: 5,217,956

[45] Date of Patent: Jun. 8, 1993

[54] COMPOSITION AND TREATMENT WITH BIOLOGICALLY ACTIVE PEPTIDES AND CERTAIN ANIONS

[75] Inventors: Michael Zasloff, Merion Station, Pa.; Wallace H. Steinberg, Rumson, N.J.

[73] Assignee: The Children's Hospital of Philadelphia, Philadelphia, Pa.

[21] Appl. No.: 798,252

[22] Filed: Oct. 29, 1991

Related U.S. Application Data

[63] Continuation of Ser. No. 476,802, Dec. 26, 1989, abandoned, which is a continuation-in-part of Ser. No. 353,618, May 18, 1989, abandoned, which is a continuation-in-part of Ser. No. 261,237, Oct. 21, 1988, abandoned.

[51] Int. Cl.$^5$ .................. A61K 37/02; C07K 7/10
[52] U.S. Cl. .................. 514/13; 514/12; 514/14; 514/21; 530/324; 530/325; 530/326; 530/350; 530/824
[58] Field of Search .................. 514/12, 13, 14, 21; 530/324, 325, 326, 350, 842

[56] References Cited

U.S. PATENT DOCUMENTS

4,507,230  3/1985  Tam et al. .................. 530/337

OTHER PUBLICATIONS

B. Christensen et al., "Channel-forming properties of cecropins and related model compounds incorporated into planar lipid membranes," *Proc. Nat.. Acad. Sci.*, vol. 85, pp. 5072–5076, Jul. 1988.

Merrifield, "Solid Phase Peptide Synthesis," *Journal of American Chemical Society*, vol. 85, pp. 2149–2154 (1963).

Zasloff, "Magainins, a class of antimicrobial peptides from Xenopus skin: Isolation, characterization of two active forms, and partial cDNA sequence of a precursor," *Proc. Natl. Acad. Sci.*, vol. 84, pp. 5449–5553 (Aug. 1987).

Hoffman et al., "A novel peptide designated PYLa and its precursor as predicted from cloned mRNA of *Xenopus laevis* skin", *The EMBO Journal*, 2:711–714, 1983.

Andreu et al., *J. Biochom.* 149:531–535, 1985.

Gibson et al., "Novel Peptide Fragments Originating from PGLa and the Caerulein and Xenopsin Precursors from *Xenopus laevis*," *J. Biol. Chem.*, 261:5341–5349, 1986.

Giovannini et al., "Biosynthesis and degratdation of peptides derived form *Xenopus laevis* prohormones," *Biochem J.* 243:113–120, 1987.

Richter, et al., "Sequence of Preprocaerulein cDNAs Cloned from Skin of *Xenopus laevis*," *J. Biol. Chem.*, 261, 3676–3680 (1986).

Wakabayashi, et al., "Complete nucleotide sequence of mRNA for caerulein precursor from Xenopus skin: the mRNA contains an unusual repetitive structure," *Nucleic Acids Research*, vol. 13, No. 6, pp. 1817–1928 (1985).

Boman, et al., "Cell-Free Immunity in Insects," *Ann Rev. Microbiol.*, vol. 41, pp. 103–126, in particular p. 108 (1987).

Selsted, et al, "Primary Structures of Three Human Neutrophil Defensins," *J. Clin. Invest.*, vol. 76, pp. 1436–1439 (1985).

Wasmoen, et al., "Biochemical and Amino Acid Sequence Analysis of Human Eosinophil Granule Major Basic Protein," *J. Biol. Chem.*, vol. 263, pp. 12559–12563 (1988).

Ooi, et al., "A 25-kDa Nh2-terminal Fragment Carries All the Antibacterial Activities of the Human Neutrophil 60-kDaBactericidal/Permeability-increasing Protein," *J. Biol. Chem.*, vol. 262, pp. 14891–14894 (1981).

Henkart, et al, "Cytolytic Activity of Purified Cytoplasmic Granules From Cytotoxic Rat Large Granular Lymphocyte Tumors," *J. Exp. Med.*, 160:75 (1984).

Podack, et al., "Cytolytic T Cell Granules," *J. Exp. Med.* 160:695 (1984).

*Primary Examiner*—Lester L. Lee
*Assistant Examiner*—Carol A. Salata
*Attorney, Agent, or Firm*—Woodcock Washburn Kurtz Mackiewicz & Norris

[57] ABSTRACT

An amphiphilic ion-channel forming peptide and a toxic anion are employed as a pharmaceutical.

23 Claims, No Drawings

COMPOSITION AND TREATMENT WITH BIOLOGICALLY ACTIVE PEPTIDES AND CERTAIN ANIONS

This application is a continuation of application Ser. No. 07/476,802, filed Dec. 26, 1989, and now abandoned, which is a continuation-in-part of the application Ser. No. 353,618, filed May 18, 1989 and now abandoned, which is a continuation-in-part of application Ser. No. 261,237, filed Oct. 21, 1988, now abandoned.

This invention relates to biologically active peptides, and more particularly to compositions and uses involving biologically active peptides and certain anions.

In accordance with an aspect of the present invention, there is provided a composition which includes at least one biologically active amphiphilic peptide and/or biologically active protein; and a toxic anion.

In accordance with another aspect of the present invention, there is provided a process wherein there is administered to a host at least one biologically active amphiphilic peptide which is an ion channel-forming peptide and/or a biologically active protein which is an ion channel forming protein; and a toxic anion.

An ion channel-forming peptide or protein or ionophore is a peptide or protein which increases the permeability for ions across a natural or synthetic lipid membrane. B. Christensen et al. PNAS vol. 85 P. 5072-76 (Jul. 1988) describes methodology which indicates whether or not a peptide or protein has ion channel-forming properties and is therefore an ionophore. As used herein an ion channel-forming peptide or ion channel forming protein is a peptide or protein which has ion channel-forming properties as determined by the method of Christensen et al.

In accordance with yet another aspect of the present invention, there is provided a method of testing, or screening a sample for ion channel-forming peptides or proteins.

In accordance with this method, a first portion of an unknown sample is contacted with a sample containing target cells (e.g., bacterial cells, fungal cells, protozoa, tumor cells, virally infected cells, etc.), and the biological activity of the sample against the particular target cells is then measured. A second portion of the unknown sample to which a quantity of fluoride ion has been added is contacted with another sample containing target cells of the same type which were contacted by the first portion of unknown sample. The biological activity of the second portion of unknown sample and fluoride ion against the target cells is then measured. If the second portion of unknown sample and fluoride ion has greater biological activity against the target cells than does the first portion, to which no fluoride ion was added, then the unknown sample contains ion channel-forming peptides or proteins. In a preferred embodiment, the target cell is a bacterium.

An amphiphilic peptide is a peptide which includes both hydrophobic and hydrophilic peptide regions.

A toxin anion is one which when introduced into a target cell inhibits and/or prevents and/or destroys the growth of the target cell.

Such a toxic anion is one which in the absence of the ion channel forming peptide or protein is unable to cross a natural or synthetic lipid membrane; in particular a cell membrane, in sufficient amounts to adversely affect a cell.

In accordance with an aspect of the present invention wherein the biologically active peptide or protein and toxic anion are administered to a host, such biologically active peptide or protein and toxic anion may be administered as a single composition or in separate compositions, and the single or separate compositions may include additional materials, actives and/or inactives, in addition to the peptide or protein and/or toxic anion.

The ion channel-forming peptides employed in the present invention are generally water soluble to a concentration of at least 20 mg/ml at neutral pH in water. In addition, such peptides are non-hemolytic; i.e., they will not rupture blood cells at effective concentrations. In addition, the structure of such peptide provides for flexibility of the peptide molecule. When the peptide is placed in water, it does not assume an amphiphilic structure. When the peptide encounters an oily surface or membrane, the peptide chain folds upon itself into a rod-like structure.

In general, such peptides have at least 16 amino acids, and preferably at least 20 amino acids. In most cases, such peptides do not have in excess of 40 amino acids.

In general, such toxic anion is employed as part of a suitable compound. As representative examples of such toxic anions, there may be mentioned: fluoride, peroxide and bicarbonate.

In employing both an ion channel-forming biologically active amphiphilic peptide or an ion channel forming protein, and a toxic anion, whether administered or prepared in a single composition, or in separate compositions, the peptide or protein and the toxic anion, are employed in amounts effective to inhibit and/or prevent and/or destroy the growth of the target cell. In effect, the anion potentiates the action of the peptide or protein. The term "potentiate," as employed herein, means that the amount of toxic anion is effective to reduce the minimum effective concentration of the peptide or protein for inhibiting growth of a target cell.

In general, the peptide or protein is employed to provide peptide dosages of from 1 mg to 500 mg per kilogram of host weight, when administered systemically. When administered topically, the peptide or protein is used in a concentration of from 0.05% to 5%.

The toxic anion, when used topically, is generally employed in a concentration of from 0.05% to 2.0%. When used systemically, the anion is generally employed in an amount of from 1 to 10 mg per kg of host weight.

The use of a combination of peptide or protein and toxic anion in accordance with the present invention is effective as an antibiotic, and may be employed to inhibit, prevent or destroy the growth or proliferation of microbes, such as bacteria and fungi. Similarly, such compositions may be employed as an anti-viral composition to inhibit, prevent or destroy the growth or proliferation of viruses.

Such compositions may also be employed as a spermicide to inhibit, prevent or destroy the motility of sperm.

Such compositions may also be employed as anti-tumor agents to inhibit the growth of or destroy tumors.

Such compositions may also be used as anti-parasitic agents to inhibit the growth of or destroy parasites.

The compositions have a broad range of potent antibiotic activity against a plurality of microorganisms, including gram-positive and gram-negative bacteria, fungi, protozoa and the like. Such compositions may be employed for treating or controlling microbial infection caused by organisms which are sensitive to such composition. The treatment may comprise administering to a host organism or tissues acceptable to or affiliated with a microbial infection an anti-microbial amount of peptide or protein and toxic anion.

The compositions may also be used as preservatives or sterilants for materials susceptible to microbial contamination.

In accordance with a preferred embodiment, the peptide used in conjunction with a toxic anion is a basic (positively charged) polypeptide having at least sixteen amino acids wherein the polypeptide includes at least eight hydrophobic amino acids and at least eight hydrophilic amino acids. Still more particularly, the hydrophobic amino acids are in groups of two adjacent amino acids, and each group of two hydrophobic amino acids is spaced from another group of two hydrophobic amino acids by at least one amino acid other than a hydrophobic amino acid (preferably at least two amino acids) and generally by no greater than four amino acids, and the amino acids between pairs of hydrophobic amino acids may or may not be hydrophilic.

The hydrophilic amino acids are generally also in groups of two adjacent amino acids in which at least one of the two amino acids is a basic hydrophilic amino acids, with such groups of two hydrophilic amino acids being spaced from each other by at least one amino acid other than a hydrophilic amino acid (preferably at least two amino acids) and generally no greater than four amino acids, and the amino acids between pairs of hydrophilic amino acids may or may not be hydrophobic.

In accordance with a particularly preferred embodiment, the polypeptide comprises a chain of at least four groups of amino acids, with each group consisting of four amino acids. Two of the four amino acids in each group are hydrophobic amino acids, and two of the four amino acids in each group are hydrophilic, with at least one of the hydrophilic amino acids in each group being a basic hydrophilic amino acid and the other being a basic or neutral hydrophilic amino acid.

The hydrophobic amino acids may be selected from the class consisting of Ala, Cys, Phe, Gly, Ile, Leu, Met, Val, Trp, and Tyr. The neutral hydrophilic amino acids may be selected from the class consisting of Asn, Gln, Ser, and Thr. The basic hydrophilic amino acids may be selected from the class consisting of Lys, Arg, His and ornithine (O).

Each of the groups of four amino acids may be of the sequence ABCD, BCDA, CDAB, or DABC, wherein A and B are each hydrophobic amino acids and may be the same or different, one of C or D is a basic hydrophilic amino acid, and the other of C or D is a basic or neutral hydrophilic amino acid and may be the same or different. In a preferred embodiment, the polypeptide chain may comprise 5 or 6 groups of this sequence. In each group, each of A, B, C and D may be the same in some or all of the groups or may be different in some or all of the groups.

The polypeptide chain preferably has at least 20 amino acids, and no greater than 50 amino acids. It is to be understood, however, that the polypeptide does not have to consist entirely of the groups described above. The polypeptide may have amino acids extending from either or both ends of the noted groups forming the polypeptide chain and/or there may be amino acids between one or more of the at least four groups and still remain within the scope of the invention.

The groups of amino acids may be repeating groups of amino acids, or the amino acids in the various groups may vary provided that in each group of the at least four groups of amino acids there are two hydrophobic and two hydrophilic amino acids as hereinabove noted.

Thus, in a preferred embodiment, the biologically active polypeptide comprises a chain including at least four groups of amino acids, each containing four amino acids. Two of the four amino acids in each group are hydrophobic, at least one amino acid is basic hydrophilic, and the remaining one is basic or neutral hydrophilic, with the polypeptide chain preferably having at least 20 amino acids but no greater than 50 amino acids.

In one embodiment, each of the at least four groups of amino acids which are in the peptide chain is of the sequence A—B—C—D, B—C—D—A, C—D—A—B or D—A—B—C wherein A and B are hydrophobic amino acids, one of C or D is basic hydrophilic amino acid, and the other of C or D is basic or neutral hydrophilic amino acid. The resulting polypeptide chain, therefore, may have one of the following sequences:

$(X_1)_a(A—B—C—D)_n(Y_1)$
$(X_2)(B—C—D—A)_n(Y_2)_b$
$(X_3)_a(C—D—A—B)_n(Y_3)_b$
$(X_4)_a(D—A—B—C)_n(Y_4)_b$ wherein $X_1$ is D; C—D— or B—C—D—, $Y_1$ is —A or —A—B or —A—B—C
$X_2$ is A—, D—A— or C—D—A—
$Y_2$ is —B, —B—C or B—C—D
$X_3$ is B—, A—B—, D—A—B—
$Y_3$ is —C, —C—D, —C—D—A
$X_4$ is C—, B—C—, A—B—C—
$Y_4$ is —D, —D—A, —D—A—B
a is 0 or 1; b is 0 or 1
and n is at least 4

It is to be understood that the peptide chain may include amino acids between the hereinabove noted groups of four amino acids provided that the spacing between such groups and the charge on the amino acids does not change the characteristics of the peptide chain which provide amphiphilicity and a positive charge and do not adversely affect the folding characteristics of the chain to that which is significantly different from one in which the hereinabove noted group of four amino acids are not spaced from each other.

As representative examples of peptides in accordance with the present invention, there may be mentioned.

I                   Ala—Phe—Ser—Lys—Ala—
Phe—Ser—Lys—Ala—Phe—Ser—Lys—Ala—
Phe—Ser—Lys—Ala—Phe—Ser—Lys
II                Ala—Phe—Ser—Lys—Ala—
Phe—Ser—Lys—Ala—Phe—Ser—Lys—Ala—
Phe—Ser—Lys—Ala—Phe—Ser—Lys—Ala—
Phe—Ser—Lys.
III   Phe—Ser—Lys—Ala—Phe—Ser—Lys—Ala—
Phe—Ser—Lys—Ala—Phe—Ser—Lys—Ala—
IV        Ser—Lys—Ala—Phe—Ser—Lys—Ala—
Phe—Ser—Lys—Ala—Phe—Ser—Lys—Ala—
Phe—Ser—Lys—Ala—Phe—
V                   Lys—Ala—Phe—Ser—Lys—Ala—
Phe—Ser—Lys—Ala—
Phe—Ser—Lys—Ala—Phe—Ser

The peptide, may have amino acids extending from either end of the chain. For example, the chains may have a Ser-Lys sequence before the "Ala" end, and/or an Ala-Phe sequence after the "Lys" end. Other amino acid sequences may also be attached to the "Ala" and/or the "lys" end.

Similarly, in any polypeptide chain having at least four groups of amino acids of the sequence as described above, the chain may have, for example, a C—D sequence before the first A—B—C—D group. Also other amino acid sequences may be attached to the "A" and/or the "D" end of one of these polypeptide chains. Also there may be amino acids in the chain which space one or more groups of the hereinabove noted four amino acids from each other.

The peptides may be produced by known techniques and obtained in substantially pure form. For example, the peptides may be synthesized on an automatic synthesizer Journal of American Chemical Society, vol. 85 Pages 2149-54 (1963). It is also possible to produce such peptides by genetic engineering techniques.

In accordance with another preferred embodiment, the peptide employed in conjunction with a toxic anion may be a magainin peptide.

A magainin peptide is either a magainin such as magainin I, II or III or an analogue or derivative thereof. The magainin peptides preferably include the following basic peptide structure $X_{12}$:

—$R_{11}$—$R_{11}$—$R_{12}$—$R_{13}$—$R_{11}$—$R_{14}$—$R_{12}$—$R_{11}$-
—$R_{14}$—$R_{12}$—$R_{11}$—$R_{11}$—$R_{11}$—$R_{14a}$—$(R_{15})_n$—$R_{14a}$-
—$R_{14}$ wherein $R_{11}$ is a hydrophobic amino acid, $R_{12}$ is a basic hydrophilic amino acid; $R_{13}$ is a hydrophobic, neutral hydrophilic, or basic hydrophilic amino acid; $R_{14}$ and $R_{14a}$ are hydrophobic or basic hydrophilic amino acids; $R_{15}$ is glutamic acid or aspartic acid, or a hydrophobic or a basic hydrophilic amino acid, and n is 0 or 1. In a preferred embodiment, $R_{13}$ is a hydrophobic or neutral hydrophilic amino acid, $R_{14a}$ is a hydrophobic amino acid, and $R_{15}$ is glutamic acid or aspartic acid.

Thus, for example, a magainin peptide may include the following structure:

—$Y_{12}$—$X_{12}$— where $X_{12}$ is the hereinabove described basic peptide structure and $Y_{12}$ is (i) $R_{12}$
(ii) $R_{14a}$—$R_{12}$
(iii) $R_{11}$—$R_{14a}$—$R_{12}$
(iv) $R_{14}$—$R_{11}$—$R_{14a}$—$R_{12}$ where $R_{11}$, $R_{12}$, $R_{14}$ and $R_{14a}$ are as previously defined.

A magainin peptide may also have the following structure:

—$X_{12}$—$Z_{12}$— wherein $X_{12}$ is as previously defined and $Z_{12}$ is:

(i) $R_{16}$ where $R_{16}$ is a basic hydrophilic amino acid or asparagine or glutamine.
(ii) $R_{16}$-$R_{17}$ where $R_{17}$ is a neutral hydrophilic amino acid, a hydrophobic amino acid, or a basic hydrophilic amino acid. Preferably, $R_{17}$ is a neutral hydrophilic amino acid.

A magainin peptide may also have the following structure:

$(Y_{12})_a$—$X_{12}$—$(Z_{12})_b$ where $X_{12}$, $Y_{12}$ and $Z_{12}$ are as previously defined and a is 0 or 1 and b is 0 or 1.

The magainin peptides may also include the following basic peptide structure $X_{13}$:

—$R_{14}$—$R_{11}$—$R_{14a}$—$R_{12}$—$R_{11}$—$R_{11}$—$R_{12}$—$R_{13}$—$R_{11}$-
—$R_{14}$—$R_{12}$—$R_{11}$—$R_{11}$—$R_{12}$—, wherein $R_{11}$, $R_{12}$, $R_{13}$, $R_{14}$, and $R_{14a}$ are amino acids as hereinabove described.

The magainin peptide may also include the following structure $X_{13}$—$Z_{13}$; wherein $X_{13}$ is the hereinabove described basic peptide structure and $Z_{13}$ is $(R_{11})_n$—$(R_{11})_n$—$(R_{11})_n$—$(R_{14a})_n$—$(R_{15})_n$—$(R_{14a})$-$_n$—$(R_{14})_n$—$(R_{16})_n$—$(R_{17})_n$ wherein $R_{11}$, $R_{14}$, $R_{14a}$, $R_{15}$, $R_{16}$, and $R_{17}$ are as hereinabove described, and n is 0 or 1, and each n may be the same or different.

The magainin peptides generally include at least fourteen amino acids and may include up to forty amino acids. A magainin peptide preferably has 22 or 23 amino acids. Accordingly, the hereinabove described basic peptide structures of a magainin peptide may include additional amino acids at the amino end or at the carboxyl end, or at both ends.

As representative examples of such magainin peptides, there may be mentioned peptides having the following primary sequence (expressed as a single letter code) as well as appropriate analogues and derivatives thereof:

(a) ($NH_2$) GIGKFLHSAGKFGKAFVGEIMKS(OH) or ($NH_2$) (Magainin I)
(b) ($NH_2$) GIGKFLHSAKKFGKAFVGEIMNS(OH) or ($N_2$) (Magainin II)
(c) ($NH_2$) GIGKFLHSAKKFGKAFVGEIMN(OH) or ($NH_2$) (Magainin III)

The following are examples of peptide derivatives or analogs of the basic structure:

(d) ($NH_2$) IGKFLHSAKKFGKAFVGEIMNS(OH) or ($NH_2$)
(e) ($NH_2$) GKFLHSAKKFGKAFVGEIMNS(OH) or ($NH_2$)
(f) ($NH_2$) KFLHSAKKFGKAFVGEIMNS(OH) or ($NH_2$)

Magainin peptides are described in *Proc. Natl. Acad Sci.* Vol. 84 pp. 5449-53 (Aug. 87). The term "magainin peptides" as used herein refers to the basic magainin structure as well as derivatives and analogs thereof, including but not limited to the representative derivatives or analogs.

In accordance with a further embodiment, the peptide employed in conjunction with a toxic anion may be a PGLa peptide or an XPF peptide.

A PGLa peptide is either PGLa or an analogue or derivative thereof. The PGLa peptides preferably include the following basic peptide structure $X_{14}$:

—$R_{11}$—$R_{17}$—$R_{12}$—$R_{11}$—$R_{14}$—$R_{14}$—$R_{11}$—$R_{11}$—$R_{14}$—$R_{12}$—$R_{11}$—$R_{11}$—$R_{12}$—$R_{11}$—$R_{11}$—$R_{11}$—$R_{12}$— where $R_{11}$, $R_{12}$, $R_{14}$, and $R_{17}$ are as previously defined.

The PGLa peptides generally include at least seventeen amino acids and may include as many as forty amino acids. Accordingly, the hereinabove described basic peptide structure for a PGLa peptide may include additional amino acids at the amino end or at the carboxyl end or at both the amino and carboxyl end.

Thus, for example, a PGLa peptide may have the following structure:

—$Y_{14}$—$X_{14}$— wherein $X_{14}$ is as previously defined and $Y_{14}$ is (i) $R_{11}$;
(ii) $R_{14}$—$R_{11}$ where $R_{11}$ and $R_{14}$ are as previously defined.

For example, a PGLa peptide may also have the following structure:

—$X_{14}$—$Z_{14}$— where $X_{14}$ is as previously defined; and $Z_{14}$ is:

(i) $R_{11}$; or (ii) $R_{11}$—$R_{11}$
where $R_{11}$ is as previously defined.

A PGLa peptide may also have the following structure:
$(Y_{14})_a$—$X_{14}$—$(Z_{14})_b$
where $X_{14}$; $Y_{14}$ and $Z_{14}$ are as previously defined, a is 0 or 1 and b is 0 or 1.

An XPF peptide is either XPF or an analogue or derivative thereof. The XPF peptides preferably include the following basic peptide structure $X_{16}$:
—$R_{11}$—$R_{17}$—$R_{12}$—$R_{11}$—$R_{14}$—$R_{18}$—$R_{17}$—$R_{11}$-
—$R_{14}$—$R_{12}$—$R_{11}$—$R_{11}$—$R_{12}$—$R_{11}$—$R_{11}$—$R_{11}$-
—$R_{12}$—$(R_{15})_n$—$R_{11}$,
wherein
$R_{11}$, $R_{12}$, $R_{14}$, $R_{15}$ and $R_{17}$ are as previously defined and $R_{18}$ is glutamine or asparagine or a basic hydrophilic, or hydrophobic amino acid and, n is 0 or 1.

The XPF peptides generally include at least nineteen amino acids and may include up to forty amino acids. Accordingly, the hereinabove described basic peptide structure of XPF may include additional amino acids at the amino end, or at the carboxyl end or at both the amino and carboxyl ends.

Thus, for example, an XPF peptide may include the following structure:
—$Y_{16}$—$X_{16}$—
where $X_{16}$ is as previously defined and $Y_{16}$ is
(i) $R_{11}$ or
(ii) $R_{14}$—$R_{11}$
where $R_{11}$ and $R_{14}$ are as previously defined.

An XPF peptide may include the following structure:
—$X_{16}$—$Z_{16}$—
where $X_{16}$ is as previously defined and $Z_{16}$ is
(i) $R_{11}$; or
(ii) $R_{11}$-$R_{18}$; or
(iii) $R_{11}$-$R_{18}$-Proline; or
(iv) $R_{11}$-$R_{18}$-Proline-$R_{12}$ An XPF peptide may also have the following structure:
$(Y_{16})_a$—$X_{16}(Z_{16})_b$
where $X_{16}$, $Y_{16}$ and $Z_{16}$ are as previously defined: a is 0 or 1 and b is 0 or 1.

Preferred are XPF or PGLa peptides, which are characterized by the following primary amino acid sequence(single letter amino acid code):
PGLa: GMASKAGAIAGKIAKVALKAL (NH$_2$)
XPF: GWASKIGQTLGKIAKVGLKELIQPK A review of XPF and PGLa can be found in Hoffman et al, *EMBO J.* 2:711-714, 1983; Andreu et al, *J. Biochem.* 149:531-535, 1985; Gibson et al *J. Biol. Chem.* 261:5341-5349, 1986; and Giovannini et al, *Biochem J.* 243:113-120, 1987.

In accordance with yet another embodiment, the peptide employed in conjunction with a toxic anion may be a CPF peptide or appropriate analogue or derivative thereof.

CPF peptides as well as analogues and derivatives thereof are herein sometimes referred to collectively as CPF peptides.

The CPF peptide is preferably one which includes the following peptide structure $X_{30}$:
—$R_{21}$—$R_{21}$—$R_{22}$—$R_{22}$—$R_{21}$—$R_{21}$—$R_{23}$—$R_{21}$—$R_{21}$-
—$R_{21}$—$R_{23}$—$R_{21}$—$R_{21}$—$R_{24}$—$R_{25}$—$R_{21}$—
wherein $R_{21}$ is a hydrophobic amino acid;
$R_{22}$ is a hydrophobic amino acid or a basic hydrophilic amino acid;
$R_{23}$ is a basic hydrophilic amino acid; and
$R_{24}$ is a hydrophobic or neutral hydrophilic amino acid; and
$R_{25}$ is a basic or neutral hydrophilic amino acid.

The hereinabove basic structure is hereinafter symbolically indicated as $X_{30}$.

The hydrophobic amino acids are Ala, Cys, Phe, Gly, Ile, Leu, Met, Val, Trp, and Tyr.

The neutral hydrophilic amino acids are Asn, Gln, Ser, and Thr.

The basic hydrophilic amino acids are Lys, Arg, His and ornithine.

The CPF peptide may include only the hereinabove noted amino acids or may include additional amino acids at the amino end or carboxyl end or both the amino and carboxyl end. In general, the peptide does not include more than 40 amino acids.

The CPF peptides including the above basic peptide structure may have from 1 to 4 additional amino acids at the amino end. Accordingly, such preferred peptides may be represented by the structural formula:
$Y_{30}$—$X_{30}$—
wherein $X_{30}$ is the hereinabove described basic peptide structure and $Y_{30}$ is
(i) $R_{25}$—, or
(ii) $R_{22}$—$R_{25}$; or
(iii) $R_{21}$—$R_{22}$—$R_{25}$; or
(iv) $R_{22}$—$R_{21}$—$R_{22}$—$R_{25}$; preferably Glycine —$R_{21}$-
—$R_{22}$—$R_{25}$—
wherein $R_{21}$, $R_{22}$, and $R_{25}$ are as previously defined.

The carboxyl end of the basic peptide structure may also have additional amino acids which may range from 1 to 13 additional amino acids.

In a preferred embodiment, the basic structure may have from 1 to 7 additional amino acids at the carboxyl end, which may be represented as follows:
—$X_{30}$—$Z_{30}$
wherein
$X_{30}$ is the hereinabove defined basic peptide structure and $Z_{30}$ is
(i) $R_{21}$—,
(ii) $R_{21}$—$R_{21}$—;
(iii) $R_{21}$—$R_{21}$—$R_{24}$;
(iv) $R_{21}$—$R_{21}$—$R_{24}$—$R_{24}$;
(v) $R_{21}$—$R_{21}$—$R_{24}$—$R_{24}$—$R_{26}$;
(vi) $R_{21}$—$R_{21}$—$R_{24}$—$R_{24}$—$R_{26}$—Gln; or
(vii) $R_{21}$—$R_{21}$—$R_{24}$—$R_{24}$—$R_{26}$—Gln—Gln,
wherein $R_{21}$ and $R_{24}$ are as previously defined, and $R_{26}$ is proline or a hydrophobic amino acid.

Preferred peptides may be represented by the following structural formula:
$(Y_{30})_a$—$X_{30}$—$(Z_{30})_b$
wherein $X_{30}$, $Y_{30}$ and $Z_{30}$ are as previously defined and a is 0 or 1 and b is 0 or 1.

Representative examples of CPF peptides which are useful in the present invention some of which have been described in the literature and comprise the following sequences (single letter amino acid code):
(1) GFGSFLGLALKAALKIGANALGGAPQQ
(2) GLASFLGKALKAGLKIGAHLLGGAPQQ
(3) GLASLLGKALKAGLKIGTHFLGGAPQQ
(4) GLASLLGKALKATLKIGTHFLGGAPQQ
(5) GFASFLGKALKAALKIGANMLGGTPQQ
(6) GFGSFLGKALKAALKIGANALGGAPQQ
(7) GFGSFLGKALKAALKIGANALGGSPQQ
(8) GFASFLGKALKAALKIGANLLGGTPQQ A review of the CPF peptides can be found in Richter, K., Egger, R., and Kreil (1986) *J. Biol. Chem.* 261, 3676-3680; Wakabayashi, T. Kato, H., and Tachibaba, S. (1985) Nucleic Acids Research 13, 1817-1828; Gibson, B. W., Poulter, L., Williams, D. H., and Maggio, J. E. (1986) J. Biol. Chem. 261, 5341-5349.

CPF peptides which may be employed in the present invention are represented by the following (single letter amino acid code):
G12S3LG4ALKA5LKIG678LGG9(10)QQ
Where:
1=F, L
2=G, A
3=F, L
4=K, L
5=A, G, T
6=A, T
7=H, N
8=A, M, F, L
9=A, S, T
10=P, L The numbered amino acids may be employed as described in any combination to provide either a basic CPF peptide structure or an analogue or derivative. The term CPF peptide includes the basic peptide structure as well as analogs or derivatives thereof.

In still another embodiment, the peptide employed in conjunction with a toxic anion is a cecropin. The cecropins and analogs and derivatives thereof are described in Ann. Rev. Microbiol 1987 Vol. 41 pages 103-26, in particular p. 108 and Christensen at al PNAS Vol. 85 p. 5072-76, which are hereby incorporated by reference.

The term cecropins includes the basic structure as well as analogues and derivatives.

In yet another embodiment, the peptide employed in conjunction with the toxic anion is a sarcotoxin. The sarcotoxins and analogs and derivatives thereof are described in Molecular Entomology pages 369-78 in particular p. 375 Alan R. Liss Inc. (1987), which is hereby incorporated by reference.

The term sarcotoxin includes the basic materials as well as analogues and derivatives.

In another embodiment, an ion channel-forming protein may be used in conjunction with a toxic anion. Ion channel-forming proteins which may be employed include defensins, also known as human neutrophil antimicrobial peptides (HNP), major basic protein (MBP) of eosinophils, bactericidal permeability-increasing protein (BPI), and a pore-forming cytotoxin called variously perforin, cytolysin, or pore-forming protein. Defensins are described in Selsted, et al., *J. Clin. Invest.*, Vol. 76, pgs. 1436-1439 (1985). MBP proteins are described in Wasmoen, et al., *J. Biol. Chem.*, Vol. 263, pgs 12559-12563. (1988). BPI proteins are described in Ooi, et al, *J. Biol. Chem.*, Vol. 262, pgs. 14891-14894 (1987). Perforin is described in Henkart, et al., *J. Exp. Med.*, 160: 75 (1984), and in Podack, et al., *J. Exp. Med.*, 160:695 (1984). The above articles are hereby incorporated by reference.

The term ion channel-forming proteins includes the basic structures of the ion-forming proteins as well as analogues and derivatives.

The present invention will be further described with respect to the following examples, however, the scope of the invention is not to be limited thereby.

TABLE 1
MINIMAL INHIBITORY CONCENTRATION (ug/ml) of AMPHIPHILIC PEPTIDES VERSUS ENTEROBACTER CLOACAE

|  | (Panel A: Absence of NaF) | (Panel B: +50 mM NaF) |
|---|---|---|
| MGN2 (Magainin II) | >500 ug/ml | 60-125 |
| PGLa | 250-500 | 60-125 |
| Z-44 | >500 | 30-60 |

TABLE II
MINIMAL INHIBITORY CONCENTRATION (ug/ml) OF AMPHIPHILIC PEPTIDES VERSUS PSEUDOMONAS AERUGINOSA

|  | (Panel A: Absence of NaF) | (Panel B: +50 mM NaF) |
|---|---|---|
| MGN2 | 250-500 | 60-125 |
| PGLa | >500 | 60-125 |
| Z-44 | 30-60 | 6-15 |

Approximately 1,000 bacteria were seeded into about 200 ul of trypticase soy broth. Either magainin 2 carboxy terminal amide, PGLa, or ALSKALSK ALSKALSKALSKALSK (Z-44) were added in increasing concentrations in the absence (Panel A) or presence (Panel B) of 50 mM NaF. As can be seen, in the absence of NaF, the MIC against *Enterobacter cloacae* exceeded 500 ug/ml for MGN2, 250 ug/ml for PGLa and 500 ug/ml for Z-44. In the presence of 50 mM NaF, the MIC against the same organism fell to between 60 to 125 ug/ml for MGN2 and PGLa, and between 30 ug/ml and 60 ug/ml for Z-44. Similar effects were noted for *Pseudomonas aeruginosa* (TABLE II).

The effect on potentiation can be demonstrated in another type of experiment (TABLE III). If $10^7$ *E. cloacae* organisms are inoculated into 1 ml of TSB in the presence of 60 ug/ml of MGN2, about $10^6$ bacteria are found to be viable on plating. If 50 mM NaF is included in the incubation containing MGN2, all bacteria are killed. The effective killing power of this antibiotic at a given concentration has been potentiated over 1 million-fold by the addition of fluoride.

TABLE III

| Addition | CFU | EOP (% viable) |
|---|---|---|
| None | $10^7$ | 100 |
| MGN2 (NH2) (60 ug/ml) | $10^6$ | 90 |
| MGN2 (NH2) (60 ug/ml) +NaF 25 mM | 0 | 0 |
| NaF 25 mM | $10^7$ | 100 |

LEGEND: Organisms were incubated in a volume of 1 ml in either trypticase soy broth alone or containing substances noted for 15 min at 37° C. An aliquot was then diluted and plated to determine number of viable organisms.

The effect of fluoride as a potentiator can be demonstrated with tumor cells. If MGN2 or Z-44 is added to minimal Eagle's medium containing 10% fetal calf serum and incubated in the presence of Vero cells (a malignant epithelial cell line) approximately 50% of the cells are rendered trypan blue permeable within 30 minute at between 250 and 500 ug/ml MGN2 or Z-44. The extent of cell damage remains relatively constant over a subsequent twenty-four hour incubation at 37° C. If NaF is added to the incubation medium containing MGN2 or Z-44, 50% killing is observed at between 125 and 250 ug/ml MGN2 or Z-44.

The peptide or protein and toxic anion, as hereinabove described, may be employed for treating a wide variety of hosts. In accordance with a preferred embodiment, a host is an animal, and such animal may be a human or non-human animal. The peptide or protein and toxic anion may be employed together in a single composition, or in separate compositions. Moreover, the toxic anion and the peptide or protein may be delivered or administered in different forms, for example, the toxic anion may be administered orally, while the peptide or protein may be administered by IV or IP.

The peptide or protein and/or toxic anion may be employed in a wide variety of pharmaceutical compositions in combination with a non-toxic pharmaceutical carrier or vehicle such as a filler, non-toxic buffer, or physiological saline solution. Such pharmaceutical compositions may be used topically or systemically and may be in any suitable form such as a liquid, solid, semi-solid, injectable solution, tablet, ointment, lotion, paste, capsule, or the like. The peptide or protein and/or toxic anion may also be used in combination with adjuvants, protease inhibitors, or compatible drugs where such a combination is seen to be desirable or advantageous in controlling infection caused by harmful microorganisms including protozoa, viruses, and the like.

The peptide(s) or protein of the present invention may be administered to a host; in particular an animal, in an effective antibiotic and/or anti-tumor and/or antiviral and/or anti-microbial and/or an antispermicidal amount and/or anti-parasitic amount in conjunction with a toxic anion for potentiating the activity of the peptide or protein.

As representative examples of administering the peptide or protein and toxic anion for topical or local administration, the peptide could be administered in an amount of up to about 1% weight to weight and the toxic anion delivered in an amount of about 50 mM (about 0.1%). Alternatively, the toxic anion, in the form of a salt such as sodium fluoride could be administered orally in conjunction with systemic administration of the peptide and/or protein. For example, the peptide or protein may be administered IV or IP to achieve a serum dose of 100 micrograms per milliliter (10 milligrams per kilogram) in conjunction with an oral dose of toxic anion, in particular, sodium fluoride of 10 meq. per kilogram.

The peptide or protein (in particular, the peptide), and toxic anion may be employed in the form of an oral composition for oral hygiene. Such a composition may be incorporated into a wide variety of composition and materials used for oral hygiene purposes, which include, but are not limited to, toothpastes, mouthwashes, tooth gels, and tooth powders. Such a composition may thus be used to treat or prevent peridontal disease, to prevent or reduce plaque, and/or to prevent or treat or reduce dental caries. The peptide or protein and toxic anion may be used to inhibit, prevent, or destroy the growth of Streptococcus mutans, which is associated with dental caries and peridontal disease.

Numerous modifications and variations of the present invention are possible in light of the above teachings and, therefore, within the scope of the appended claims, the invention may be practiced otherwise than as particularly described.

What is claimed is:

1. A process for inhibiting growth of a target cell or virus, comprising:
administering to a host at least one biologically active amphiphilic peptide and/or biologically active protein, said peptide or protein being an ion channel-forming peptide or protein; and a toxic anion, said components being administered in an amount effective in inhibiting growth of a target cell or virus in a host.

2. The process of claim 1 wherein the peptide is a magainin peptide.

3. The process of claim 1 wherein the peptide is a cecropin.

4. The process of claim 1 wherein the peptide is a sarcotoxin.

5. The process of claim 1 wherein the peptide is a XPF peptide.

6. The process of claim 1 wherein the peptide is a PGLa peptide.

7. The process of claim 1 wherein the peptide is a CPF peptide.

8. The process of claim 1 wherein the toxic anion is selected from the group consisting of fluoride, bicarbonate and peroxide.

9. The process of claim 1 wherein the anion is fluoride.

10. The process of claim 1 wherein the peptide and fluoride are administered separately.

11. The process of claim 9 wherein the fluoride is administered topically.

12. The process of claim 9 wherein the peptide is administered topically.

13. The process of claim 9 wherein the peptide and fluoride are both administered topically.

14. The process of claim 9 wherein the peptide and fluoride are administered in effective antibiotic amounts.

15. A composition comprising:
(a) at least one biologically active amphiphilic peptide and/or biologically active protein, said peptide or protein being an ion channel-forming peptide or protein; and
(b) a toxic anion.

16. The composition of claim 15 wherein said components (a) and (b) are present in an amount effective in inhibiting growth of a target cell or virus.

17. The composition of claim 15 wherein the anion is fluoride.

18. The composition of claim 17 wherein the peptide is a magainin peptide.

19. The composition of claim 17 wherein the peptide is a cecropin.

20. The composition of claim 17 wherein the peptide is a sarcotoxin.

21. The composition of claim 17 wherein the peptide is a XPF peptide.

22. The composition of claim 17 wherein the peptide is a PGLa peptide.

23. The composition of claim 17 wherein the peptide is a CPF peptide.

* * * * *